(12) United States Patent
Averbuch

(10) Patent No.: US 8,473,032 B2
(45) Date of Patent: *Jun. 25, 2013

(54) FEATURE-BASED REGISTRATION METHOD

(75) Inventor: Dorian Averbuch, Ramat HaSharon (IL)

(73) Assignee: Superdimension, Ltd., Herzliya (IL)

( * ) Notice: Subject to any disclaimer, the term of this patent is extended or adjusted under 35 U.S.C. 154(b) by 471 days.

This patent is subject to a terminal disclaimer.

(21) Appl. No.: 12/476,976

(22) Filed: Jun. 2, 2009

(65) Prior Publication Data

US 2010/0030064 A1  Feb. 4, 2010

Related U.S. Application Data

(60) Provisional application No. 61/058,470, filed on Jun. 3, 2008.

(51) Int. Cl.
*A61B 5/05* (2006.01)
*G06K 9/00* (2006.01)
*G06K 9/34* (2006.01)

(52) U.S. Cl.
USPC ............ 600/424; 600/427; 382/131; 382/173

(58) Field of Classification Search
USPC .................. 600/407, 424, 427, 160; 382/131, 382/154, 173
See application file for complete search history.

(56) References Cited

U.S. PATENT DOCUMENTS

| | | | |
|---|---|---|---|
| 1,576,781 A | 3/1926 | Phillips | |
| 1,735,726 A | 11/1929 | Bornhardt | |
| 2,407,845 A | 9/1946 | Nemeyer | |
| 2,650,588 A | 9/1953 | Drew | |
| 2,697,433 A | 12/1954 | Sehnder | |
| 3,016,899 A | 1/1962 | Stenvall | |
| 3,017,887 A | 1/1962 | Heyer | |
| 3,061,936 A | 11/1962 | Dobbeleer | |
| 3,073,310 A | 1/1963 | Mocarski | |
| 3,109,588 A | 11/1963 | Polhemus et al. | |
| 3,121,228 A | 2/1964 | Kalmus | |
| 3,294,083 A | 12/1966 | Alderson | |
| 3,367,326 A | 2/1968 | Frazier | |

(Continued)

FOREIGN PATENT DOCUMENTS

| CA | 964149 | 3/1975 |
|---|---|---|
| DE | 30 42 343 A1 | 6/1982 |

(Continued)

OTHER PUBLICATIONS

United States Patent and Trademark Office, Final Office Action mailed May 1, 2012 in U.S. Appl. No. 12/476,976, 6 pages.

(Continued)

*Primary Examiner* — Michael Rozanski
(74) *Attorney, Agent, or Firm* — Carter, DeLuca, Farrell & Schmidt, LLP

(57) ABSTRACT

Methods for registering a three-dimensional model of a body volume to a real-time indication of a sensor position that involve analyzing scanned and sensed voxels and using parameters or thresholds to identify said voxels as being either tissue or intraluminal fluid. Those voxels identified as fluid are then used to construct a real-time sensed three-dimensional model of the lumen which is then compared to a similarly constructed, but previously scanned model to establish and update registration.

33 Claims, 2 Drawing Sheets

U.S. PATENT DOCUMENTS

| | | |
|---|---|---|
| 3,439,256 A | 4/1969 | Kahne et al. |
| 3,519,436 A | 7/1970 | Bauer et al. |
| 3,577,160 A | 5/1971 | White |
| 3,600,625 A | 8/1971 | Tsuneta et al. |
| 3,605,725 A | 9/1971 | Bentov |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,822,697 A | 7/1974 | Komiya |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,135,184 A | 1/1979 | Pruzick |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,249,167 A | 2/1981 | Purinton et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,308,530 A | 12/1981 | Kip et al. |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,341,385 A | 7/1982 | Doyle et al. |
| 4,346,384 A | 8/1982 | Raab |
| 4,358,856 A | 11/1982 | Stivender et al. |
| 4,368,536 A | 1/1983 | Pfeiler |
| 4,394,831 A | 7/1983 | Egli et al. |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,425,511 A | 1/1984 | Brosh |
| 4,431,005 A | 2/1984 | McCormick |
| 4,447,224 A | 5/1984 | Decant, Jr. et al. |
| 4,447,462 A | 5/1984 | Tafuri et al. |
| 4,485,815 A | 12/1984 | Amplatz |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,587,975 A | 5/1986 | Salo et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,686,695 A | 8/1987 | Macovski |
| 4,688,037 A | 8/1987 | Krieg |
| 4,696,544 A | 9/1987 | Costella |
| 4,697,595 A | 10/1987 | Breyer et al. |
| 4,701,049 A | 10/1987 | Beckmann et al. |
| 4,704,602 A | 11/1987 | Asbrink |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,726,355 A | 2/1988 | Okada |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,784,117 A | 11/1988 | Miyazaki |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,250 A | 5/1989 | Rotier |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl et al. |
| 4,923,459 A | 5/1990 | Nambu |
| 4,931,056 A | 6/1990 | Ghajar et al. |
| 4,945,305 A | 7/1990 | Blood |
| 4,945,912 A | 8/1990 | Langberg |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,047 A | 5/1991 | Schwab |

| | | | | | |
|---|---|---|---|---|---|
| 5,013,317 A | 5/1991 | Cole et al. | 5,262,722 A | 11/1993 | Hedengren et al. |
| 5,016,639 A | 5/1991 | Allen | 5,265,610 A | 11/1993 | Darrow et al. |
| 5,017,139 A | 5/1991 | Mushabac | 5,265,611 A | 11/1993 | Hoenig et al. |
| 5,023,102 A | 6/1991 | Given | 5,269,759 A | 12/1993 | Hernandez et al. |
| 5,027,818 A | 7/1991 | Bova et al. | 5,271,400 A | 12/1993 | Dumoulin et al. |
| 5,030,196 A | 7/1991 | Inoue | 5,273,025 A | 12/1993 | Sakiyama et al. |
| 5,030,222 A | 7/1991 | Calandruccio et al. | 5,274,551 A | 12/1993 | Corby, Jr. |
| 5,031,203 A | 7/1991 | Trecha | 5,279,309 A | 1/1994 | Taylor et al. |
| RE33,662 E | 8/1991 | Blair et al. | 5,285,787 A | 2/1994 | Machida |
| 5,042,486 A | 8/1991 | Pfeiler et al. | 5,291,199 A | 3/1994 | Overman et al. |
| 5,047,036 A | 9/1991 | Koutrouvelis | 5,291,889 A | 3/1994 | Kenet et al. |
| 5,050,608 A | 9/1991 | Watanabe et al. | 5,295,483 A | 3/1994 | Nowacki et al. |
| 5,054,492 A | 10/1991 | Scribner et al. | 5,297,549 A | 3/1994 | Beatty et al. |
| 5,057,095 A | 10/1991 | Fabian | 5,299,253 A | 3/1994 | Wessels |
| 5,059,789 A | 10/1991 | Salcudean | 5,299,254 A | 3/1994 | Dancer et al. |
| 5,070,462 A | 12/1991 | Chau | 5,299,288 A | 3/1994 | Glassman et al. |
| 5,078,140 A | 1/1992 | Kwoh | 5,300,080 A | 4/1994 | Clayman et al. |
| 5,079,699 A | 1/1992 | Tuy et al. | 5,301,061 A | 4/1994 | Nakada et al. |
| 5,082,286 A | 1/1992 | Ryan et al. | 5,305,091 A | 4/1994 | Gelbart et al. |
| 5,086,401 A | 2/1992 | Glassman et al. | 5,305,203 A | 4/1994 | Raab |
| 5,088,928 A | 2/1992 | Chan | 5,306,271 A | 4/1994 | Zinreich et al. |
| 5,094,241 A | 3/1992 | Allen | 5,307,072 A | 4/1994 | Jones, Jr. |
| 5,097,839 A | 3/1992 | Allen | 5,307,816 A | 5/1994 | Hashimoto et al. |
| 5,098,426 A | 3/1992 | Sklar et al. | 5,309,913 A | 5/1994 | Kormos et al. |
| 5,099,845 A | 3/1992 | Besz et al. | 5,315,630 A | 5/1994 | Sturm et al. |
| 5,099,846 A | 3/1992 | Hardy | 5,316,024 A | 5/1994 | Hirschi et al. |
| 5,104,393 A | 4/1992 | Isner et al. | 5,318,025 A | 6/1994 | Dumoulin et al. |
| 5,105,829 A | 4/1992 | Fabian et al. | 5,320,111 A | 6/1994 | Livingston |
| 5,107,839 A | 4/1992 | Houdek et al. | 5,325,728 A | 7/1994 | Zimmerman et al. |
| 5,107,843 A | 4/1992 | Aarnio et al. | 5,325,873 A | 7/1994 | Hirschi et al. |
| 5,107,862 A | 4/1992 | Fabian et al. | 5,327,889 A | 7/1994 | Imran |
| 5,109,194 A | 4/1992 | Cantaloube | 5,329,944 A | 7/1994 | Fabian et al. |
| 5,119,817 A | 6/1992 | Allen | 5,330,485 A | 7/1994 | Clayman et al. |
| 5,127,408 A | 7/1992 | Parsons et al. | 5,333,168 A | 7/1994 | Fernandes et al. |
| 5,129,654 A | 7/1992 | Bogner | 5,341,807 A | 8/1994 | Nardella |
| 5,142,930 A | 9/1992 | Allen et al. | 5,347,289 A | 9/1994 | Elhardt |
| 5,143,076 A | 9/1992 | Hardy et al. | 5,353,795 A | 10/1994 | Souza et al. |
| 5,152,277 A | 10/1992 | Honda et al. | 5,353,800 A | 10/1994 | Pohndorf et al. |
| 5,152,288 A | 10/1992 | Hoenig et al. | 5,353,807 A | 10/1994 | DeMarco |
| 5,160,337 A | 11/1992 | Cosman | 5,357,253 A | 10/1994 | Van Etten et al. |
| 5,161,536 A | 11/1992 | Vilkomerson et al. | 5,359,417 A | 10/1994 | Muller et al. |
| 5,178,130 A | 1/1993 | Kaiya | 5,368,030 A | 11/1994 | Zinreich et al. |
| 5,178,164 A | 1/1993 | Allen | 5,371,778 A | 12/1994 | Yanof et al. |
| 5,178,621 A | 1/1993 | Cook et al. | 5,375,596 A | 12/1994 | Twiss et al. |
| 5,186,174 A | 2/1993 | Schlondorff et al. | 5,376,795 A | 12/1994 | Hasegawa et al. |
| 5,187,475 A | 2/1993 | Wagener et al. | 5,377,678 A | 1/1995 | Dumoulin et al. |
| 5,188,126 A | 2/1993 | Fabian et al. | 5,383,454 A | 1/1995 | Bucholz |
| 5,188,368 A | 2/1993 | Ryan | 5,383,852 A | 1/1995 | Stevens-Wright |
| 5,190,059 A | 3/1993 | Fabian et al. | 5,385,146 A | 1/1995 | Goldreyer |
| 5,190,285 A | 3/1993 | Levy et al. | 5,385,148 A | 1/1995 | Lesh et al. |
| 5,193,106 A | 3/1993 | DeSena | 5,386,828 A | 2/1995 | Owens et al. |
| 5,196,928 A | 3/1993 | Karasawa et al. | 5,389,073 A | 2/1995 | Imran |
| 5,197,476 A | 3/1993 | Nowacki et al. | 5,389,101 A | 2/1995 | Heilbrun et al. |
| 5,197,965 A | 3/1993 | Cherry et al. | 5,391,199 A | 2/1995 | Ben-Haim |
| 5,198,768 A | 3/1993 | Keren | 5,394,457 A | 2/1995 | Leibinger et al. |
| 5,198,877 A | 3/1993 | Schulz | 5,394,875 A | 3/1995 | Lewis et al. |
| 5,203,337 A | 4/1993 | Feldman | 5,397,321 A | 3/1995 | Houser et al. |
| 5,207,688 A | 5/1993 | Carol | 5,397,329 A | 3/1995 | Allen |
| 5,211,164 A | 5/1993 | Allen | 5,398,684 A | 3/1995 | Hardy |
| 5,211,165 A | 5/1993 | Dumoulin et al. | 5,398,691 A | 3/1995 | Martin et al. |
| 5,211,176 A | 5/1993 | Ishiguro et al. | 5,399,146 A | 3/1995 | Nowacki et al. |
| 5,212,720 A | 5/1993 | Landi et al. | 5,400,384 A | 3/1995 | Fernandes et al. |
| 5,214,615 A | 5/1993 | Bauer | 5,400,771 A | 3/1995 | Pirak et al. |
| 5,219,351 A | 6/1993 | Teubner et al. | 5,402,801 A | 4/1995 | Taylor |
| 5,222,499 A | 6/1993 | Allen et al. | 5,405,346 A | 4/1995 | Grundy et al. |
| 5,224,049 A | 6/1993 | Mushabac | 5,408,409 A | 4/1995 | Glassman et al. |
| 5,228,442 A | 7/1993 | Imran | 5,409,000 A | 4/1995 | Imran |
| 5,230,338 A | 7/1993 | Allen et al. | 5,413,573 A | 5/1995 | Koivukangas |
| 5,230,623 A | 7/1993 | Guthrie et al. | 5,417,210 A | 5/1995 | Funda et al. |
| 5,233,990 A | 8/1993 | Barnea | 5,419,325 A | 5/1995 | Dumoulin et al. |
| 5,237,996 A | 8/1993 | Waldman et al. | 5,423,334 A | 6/1995 | Jordan |
| 5,249,581 A | 10/1993 | Horbal et al. | 5,425,367 A | 6/1995 | Shapiro et al. |
| 5,251,127 A | 10/1993 | Raab | 5,425,382 A | 6/1995 | Golden et al. |
| 5,251,635 A | 10/1993 | Dumoulin et al. | 5,426,683 A | 6/1995 | O'Farrell, Jr. et al. |
| 5,253,647 A | 10/1993 | Takahashi et al. | 5,426,687 A | 6/1995 | Goodall et al. |
| 5,255,680 A | 10/1993 | Darrow et al. | 5,427,097 A | 6/1995 | Depp |
| 5,257,636 A | 11/1993 | White | 5,429,132 A | 7/1995 | Guy et al. |
| 5,257,998 A | 11/1993 | Ota et al. | 5,433,198 A | 7/1995 | Desai |
| 5,261,404 A | 11/1993 | Mick et al. | 5,435,573 A | 7/1995 | Oakford |

| | | |
|---|---|---|
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,447,156 A | 9/1995 | Dumoulin et al. |
| 5,448,610 A | 9/1995 | Yamamoto et al. |
| 5,453,686 A | 9/1995 | Anderson |
| 5,456,254 A | 10/1995 | Pietroski et al. |
| 5,456,664 A | 10/1995 | Heinzelman et al. |
| 5,456,689 A | 10/1995 | Kresch et al. |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,472,441 A | 12/1995 | Edwards et al. |
| 5,476,100 A | 12/1995 | Galel |
| 5,476,495 A | 12/1995 | Kordis et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,492,131 A | 2/1996 | Galel |
| 5,492,713 A | 2/1996 | Sommermeyer |
| 5,493,517 A | 2/1996 | Frazier |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,515,853 A | 5/1996 | Smith et al. |
| 5,517,990 A | 5/1996 | Kalfas et al. |
| 5,520,059 A | 5/1996 | Garshelis |
| 5,522,814 A | 6/1996 | Bernaz |
| 5,522,815 A | 6/1996 | Durgin, Jr. et al. |
| 5,531,227 A | 7/1996 | Schneider |
| 5,531,520 A | 7/1996 | Grimson et al. |
| 5,531,686 A | 7/1996 | Lundquist et al. |
| 5,542,938 A | 8/1996 | Avellanet et al. |
| 5,543,951 A | 8/1996 | Moehrmann |
| 5,545,200 A | 8/1996 | West et al. |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,555,883 A | 9/1996 | Avitall |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,033 A | 12/1996 | Yeung |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,599,305 A | 2/1997 | Hermann et al. |
| 5,600,330 A | 2/1997 | Blood |
| 5,603,318 A | 2/1997 | Heilbrun et al. |
| 5,606,975 A | 3/1997 | Liang et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,620,734 A | 4/1997 | Wesdorp et al. |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,634 A | 6/1997 | Kordis et al. |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,646,525 A | 7/1997 | Gilboa |
| 5,647,361 A | 7/1997 | Damadian |
| 5,651,047 A | 7/1997 | Moorman et al. |
| 5,660,865 A | 8/1997 | Pedersen et al. |
| 5,662,108 A | 9/1997 | Budd et al. |
| 5,662,111 A | 9/1997 | Cosman |
| 5,664,001 A | 9/1997 | Tachibana et al. |
| 5,668,844 A | 9/1997 | Webber |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,701,898 A | 12/1997 | Adam et al. |
| 5,702,406 A | 12/1997 | Vilsmeier et al. |
| 5,704,361 A | 1/1998 | Seward et al. |
| 5,711,299 A | 1/1998 | Manwaring et al. |
| 5,713,369 A | 2/1998 | Tao et al. |
| 5,713,853 A | 2/1998 | Clark et al. |
| 5,713,946 A | 2/1998 | Ben-Haim |
| 5,715,822 A | 2/1998 | Watkins |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,740,808 A | 4/1998 | Panescu et al. |
| 5,741,214 A | 4/1998 | Ouchi et al. |
| 5,741,320 A | 4/1998 | Thornton et al. |
| 5,742,394 A | 4/1998 | Hansen |
| 5,744,802 A | 4/1998 | Muehllehner et al. |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,752,518 A | 5/1998 | McGee et al. |
| 5,755,725 A | 5/1998 | Druais |
| RE35,816 E | 6/1998 | Schulz |
| 5,758,667 A | 6/1998 | Slettenmark |
| 5,760,335 A | 6/1998 | Gilboa |
| 5,762,064 A | 6/1998 | Polyani |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |

| Patent No. | Date | Inventor(s) |
|---|---|---|
| 5,772,594 A | 6/1998 | Barrick |
| 5,775,322 A | 7/1998 | Silverstein et al. |
| 5,776,050 A | 7/1998 | Chen et al. |
| 5,776,064 A | 7/1998 | Kalfas et al. |
| 5,782,765 A | 7/1998 | Jonkman |
| 5,782,828 A | 7/1998 | Chen et al. |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,084 A | 9/1998 | Olson |
| 5,803,089 A | 9/1998 | Ferre et al. |
| 5,807,252 A | 9/1998 | Hassfeld et al. |
| 5,810,007 A | 9/1998 | Holupka et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,837,001 A | 11/1998 | Mackey |
| 5,840,024 A | 11/1998 | Taniguchi et al. |
| 5,840,025 A | 11/1998 | Ben Haim |
| 5,842,984 A | 12/1998 | Avitall |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,853,327 A | 12/1998 | Gilboa |
| 5,857,997 A | 1/1999 | Cimino et al. |
| 5,865,726 A | 2/1999 | Katsurada et al. |
| 5,865,846 A | 2/1999 | Bryan et al. |
| 5,868,673 A | 2/1999 | Vesely |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,871,523 A | 2/1999 | Fleischman et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,134 A | 4/1999 | Goble et al. |
| 5,891,157 A | 4/1999 | Day et al. |
| 5,893,885 A | 4/1999 | Webster, Jr. |
| 5,899,860 A | 5/1999 | Pfeiffer et al. |
| 5,902,239 A | 5/1999 | Buurman |
| 5,902,324 A | 5/1999 | Thompson et al. |
| 5,904,691 A | 5/1999 | Barnett et al. |
| 5,907,395 A | 5/1999 | Schulz et al. |
| 5,909,476 A | 6/1999 | Cheng et al. |
| 5,913,820 A | 6/1999 | Bladen et al. |
| 5,916,210 A | 6/1999 | Winston |
| 5,919,147 A | 7/1999 | Jain |
| 5,919,188 A | 7/1999 | Shearon et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,930,329 A | 7/1999 | Navab |
| 5,935,160 A | 8/1999 | Auricchio et al. |
| 5,938,585 A | 8/1999 | Donofrio |
| 5,938,602 A | 8/1999 | Lloyd |
| 5,938,603 A | 8/1999 | Ponzi |
| 5,938,694 A | 8/1999 | Jaraczewski et al. |
| 5,941,251 A | 8/1999 | Panescu et al. |
| 5,944,023 A | 8/1999 | Johnson et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,461 A | 9/1999 | Nyo et al. |
| 5,951,475 A | 9/1999 | Gueziec et al. |
| 5,951,571 A | 9/1999 | Audette |
| 5,954,647 A | 9/1999 | Bova et al. |
| 5,954,649 A | 9/1999 | Chia et al. |
| 5,954,796 A | 9/1999 | McCarty et al. |
| 5,957,844 A | 9/1999 | Dekel et al. |
| 5,966,090 A | 10/1999 | McEwan |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,127 A | 11/1999 | Lax |
| 5,976,156 A | 11/1999 | Taylor et al. |
| 5,980,504 A | 11/1999 | Sharkey et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,724 A | 2/2000 | Gronningsaeter et al. |
| 6,019,725 A | 2/2000 | Vesely et al. |
| 6,019,728 A | 2/2000 | Iwata et al. |
| 6,022,578 A | 2/2000 | Miller |
| 6,024,695 A | 2/2000 | Taylor et al. |
| 6,024,739 A | 2/2000 | Ponzi et al. |
| 6,032,675 A | 3/2000 | Rubinsky |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,064,390 A | 5/2000 | Sagar et al. |
| 6,071,288 A | 6/2000 | Carol et al. |
| 6,073,043 A | 6/2000 | Schneider |
| 6,076,008 A | 6/2000 | Bucholz |
| 6,077,257 A | 6/2000 | Edwards et al. |
| 6,096,036 A | 8/2000 | Bowe et al. |
| 6,096,050 A | 8/2000 | Audette |
| 6,104,294 A | 8/2000 | Andersson et al. |
| 6,104,944 A | 8/2000 | Martinelli |
| 6,106,517 A | 8/2000 | Zupkas |
| 6,112,111 A | 8/2000 | Glantz |
| 6,115,626 A | 9/2000 | Whayne et al. |
| 6,117,476 A | 9/2000 | Eger et al. |
| 6,118,845 A | 9/2000 | Simon et al. |
| 6,122,538 A | 9/2000 | Sliwa, Jr. et al. |
| 6,122,541 A | 9/2000 | Cosman et al. |
| 6,123,979 A | 9/2000 | Hepburn et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,179,809 B1 | 1/2001 | Khairkhahan et al. |
| 6,183,444 B1 | 2/2001 | Glines et al. |

| Patent | Kind | Date | Name |
|---|---|---|---|
| 6,188,355 | B1 | 2/2001 | Gilboa |
| 6,192,280 | B1 | 2/2001 | Sommer et al. |
| 6,194,639 | B1 | 2/2001 | Botella et al. |
| 6,201,387 | B1 | 3/2001 | Govari |
| 6,203,493 | B1 | 3/2001 | Ben-Haim |
| 6,203,497 | B1 | 3/2001 | Dekel et al. |
| 6,208,884 | B1 | 3/2001 | Kumar et al. |
| 6,210,362 | B1 | 4/2001 | Ponzi |
| 6,211,666 | B1 | 4/2001 | Acker |
| 6,213,995 | B1 | 4/2001 | Steen et al. |
| 6,213,998 | B1 | 4/2001 | Shen et al. |
| 6,216,027 | B1 | 4/2001 | Willis et al. |
| 6,216,029 | B1 | 4/2001 | Paltieli |
| 6,223,067 | B1 | 4/2001 | Vilsmeier |
| 6,226,543 | B1 | 5/2001 | Gilboa et al. |
| 6,233,476 | B1 | 5/2001 | Strommer et al. |
| 6,236,875 | B1 | 5/2001 | Bucholz et al. |
| 6,245,020 | B1 | 6/2001 | Moore et al. |
| 6,246,231 | B1 | 6/2001 | Ashe |
| 6,246,784 | B1 | 6/2001 | Summers et al. |
| 6,246,898 | B1 | 6/2001 | Vesely et al. |
| 6,246,899 | B1 | 6/2001 | Chia et al. |
| 6,248,074 | B1 | 6/2001 | Ohno et al. |
| 6,253,770 | B1 | 7/2001 | Acker et al. |
| 6,259,942 | B1 | 7/2001 | Westermann et al. |
| 6,264,654 | B1 | 7/2001 | Swartz et al. |
| 6,272,371 | B1 | 8/2001 | Shlomo |
| 6,273,896 | B1 | 8/2001 | Franck et al. |
| 6,285,902 | B1 | 9/2001 | Kienzle, III et al. |
| 6,289,235 | B1 | 9/2001 | Webber et al. |
| 6,298,262 | B1 | 10/2001 | Franck et al. |
| 6,304,769 | B1 | 10/2001 | Arenson et al. |
| 6,306,097 | B1 | 10/2001 | Park et al. |
| 6,314,310 | B1 | 11/2001 | Ben-Haim et al. |
| 6,319,250 | B1 | 11/2001 | Falwell et al. |
| 6,331,116 | B1 | 12/2001 | Kaufman et al. |
| 6,331,156 | B1 | 12/2001 | Haefele et al. |
| 6,332,089 | B1 | 12/2001 | Acker et al. |
| 6,335,617 | B1 | 1/2002 | Osadchy et al. |
| 6,341,231 | B1 | 1/2002 | Ferre et al. |
| 6,345,112 | B1 | 2/2002 | Summers et al. |
| 6,346,940 | B1 | 2/2002 | Fukunaga |
| 6,351,513 | B1 | 2/2002 | Bani-Hashemi et al. |
| 6,351,659 | B1 | 2/2002 | Vilsmeier |
| 6,366,799 | B1 | 4/2002 | Acker et al. |
| 6,373,240 | B1 | 4/2002 | Govari |
| 6,380,732 | B1 | 4/2002 | Gilboa |
| 6,381,485 | B1 | 4/2002 | Hunter et al. |
| 6,383,144 | B1 | 5/2002 | Mooney et al. |
| 6,405,072 | B1 | 6/2002 | Cosman |
| 6,423,009 | B1 | 7/2002 | Downey et al. |
| 6,424,856 | B1 | 7/2002 | Vilsmeier et al. |
| 6,427,314 | B1 | 8/2002 | Acker |
| 6,428,547 | B1 | 8/2002 | Vilsmeier et al. |
| 6,434,415 | B1 | 8/2002 | Foley et al. |
| 6,437,567 | B1 | 8/2002 | Schenck et al. |
| 6,443,894 | B1 | 9/2002 | Sumanaweera et al. |
| 6,445,943 | B1 | 9/2002 | Ferre et al. |
| 6,447,504 | B1 | 9/2002 | Ben-Haim et al. |
| 6,453,190 | B1 | 9/2002 | Acker et al. |
| 6,468,265 | B1 | 10/2002 | Evans et al. |
| 6,470,207 | B1 | 10/2002 | Simon et al. |
| 6,473,635 | B1 | 10/2002 | Rasche |
| 6,474,341 | B1 | 11/2002 | Hunter et al. |
| 6,478,802 | B2 | 11/2002 | Kienzle, III et al. |
| 6,484,049 | B1 | 11/2002 | Seeley et al. |
| 6,484,118 | B1 | 11/2002 | Govari |
| 6,490,475 | B1 | 12/2002 | Seeley et al. |
| 6,493,573 | B1 | 12/2002 | Martinelli et al. |
| 6,498,477 | B1 | 12/2002 | Govari et al. |
| 6,498,944 | B1 | 12/2002 | Ben-Haim et al. |
| 6,499,488 | B1 | 12/2002 | Hunter et al. |
| 6,516,046 | B1 | 2/2003 | Frohlich et al. |
| 6,517,534 | B1 | 2/2003 | McGovern et al. |
| 6,527,443 | B1 | 3/2003 | Vilsmeier et al. |
| 6,551,325 | B2 | 4/2003 | Neubauer et al. |
| 6,556,696 | B1 | 4/2003 | Summers et al. |
| 6,558,333 | B2 | 5/2003 | Gilboa et al. |
| 6,574,492 | B1 | 6/2003 | Ben-Haim et al. |
| 6,574,498 | B1 | 6/2003 | Gilboa |
| 6,580,938 | B1 | 6/2003 | Acker |
| 6,584,174 | B2 | 6/2003 | Schubert et al. |
| 6,585,763 | B1 | 7/2003 | Keilman et al. |
| 6,591,129 | B1 | 7/2003 | Ben-Haim et al. |
| 6,593,884 | B1 | 7/2003 | Gilboa et al. |
| 6,609,022 | B2 | 8/2003 | Vilsmeier et al. |
| 6,611,700 | B1 | 8/2003 | Vilsmeier et al. |
| 6,615,155 | B2 | 9/2003 | Gilboa |
| 6,618,612 | B1 | 9/2003 | Acker et al. |
| 6,628,980 | B2 | 9/2003 | Atalar |
| 6,640,128 | B2 | 10/2003 | Vilsmeier et al. |
| 6,650,927 | B1 | 11/2003 | Keidar |
| 6,666,864 | B2 | 12/2003 | Bencini et al. |
| 6,676,659 | B2 | 1/2004 | Hutchins et al. |
| 6,690,816 | B2 | 2/2004 | Aylward et al. |
| 6,690,963 | B2 | 2/2004 | Ben-Haim et al. |
| 6,694,162 | B2 | 2/2004 | Hartlep |
| 6,701,179 | B1 | 3/2004 | Martinelli et al. |
| 6,702,780 | B1 | 3/2004 | Gilboa et al. |
| 6,706,041 | B1 | 3/2004 | Costantino |
| 6,711,429 | B1 | 3/2004 | Gilboa et al. |
| 6,735,465 | B2 | 5/2004 | Panescu |
| 6,751,492 | B2 | 6/2004 | Ben-Haim |
| 6,770,070 | B1 | 8/2004 | Balbierz |
| 6,788,967 | B2 | 9/2004 | Ben-Haim et al. |
| 6,796,963 | B2 | 9/2004 | Carpenter et al. |
| 6,810,281 | B2 | 10/2004 | Brock et al. |
| 6,833,814 | B2 | 12/2004 | Gilboa et al. |
| 6,887,236 | B2 | 5/2005 | Gilboa |
| 6,947,788 | B2 | 9/2005 | Gilboa et al. |
| 6,976,013 | B1 | 12/2005 | Mah |
| 6,995,729 | B2 | 2/2006 | Govari et al. |
| 6,996,430 | B1 | 2/2006 | Gilboa et al. |
| 7,033,325 | B1 | 4/2006 | Sullivan |
| 7,176,936 | B2 | 2/2007 | Sauer et al. |
| 7,197,354 | B2 | 3/2007 | Sobe |
| 7,233,820 | B2 | 6/2007 | Gilboa |
| 7,236,567 | B2 | 6/2007 | Sandkamp et al. |
| 7,286,868 | B2 | 10/2007 | Govari |
| 7,301,332 | B2 | 11/2007 | Govari et al. |
| 7,321,228 | B2 | 1/2008 | Govari |
| 7,324,915 | B2 | 1/2008 | Altmann et al. |
| 7,343,195 | B2 | 3/2008 | Strommer et al. |
| 7,353,125 | B2 | 4/2008 | Nieminen et al. |
| 7,357,795 | B2 | 4/2008 | Kaji et al. |
| 7,366,562 | B2 | 4/2008 | Dukesherer et al. |
| 7,370,656 | B2 | 5/2008 | Gleich et al. |
| 7,373,271 | B1 | 5/2008 | Schneider |
| 7,386,339 | B2 | 6/2008 | Strommer et al. |
| 7,397,364 | B2 | 7/2008 | Govari |
| 7,399,296 | B2 | 7/2008 | Poole et al. |
| 7,420,468 | B2 | 9/2008 | Fabian et al. |
| 7,497,029 | B2 | 3/2009 | Plassky et al. |
| 7,505,809 | B2 | 3/2009 | Strommer et al. |
| 7,517,318 | B2 | 4/2009 | Altmann et al. |
| 7,536,218 | B2 | 5/2009 | Govari et al. |
| 7,555,330 | B2 | 6/2009 | Gilboa et al. |
| RE40,852 | E | 7/2009 | Martinelli et al. |
| 7,570,987 | B2 | 8/2009 | Raabe et al. |
| 7,577,474 | B2 | 8/2009 | Vilsmeier |
| 7,579,837 | B2 | 8/2009 | Fath et al. |
| 7,587,235 | B2 | 9/2009 | Wist et al. |
| 7,599,535 | B2 | 10/2009 | Kiraly et al. |
| 7,599,810 | B2 | 10/2009 | Yamazaki |
| 7,630,753 | B2 | 12/2009 | Simon et al. |
| 7,634,122 | B2 | 12/2009 | Bertram et al. |
| 7,636,595 | B2 | 12/2009 | Marquart et al. |
| 7,641,609 | B2 | 1/2010 | Ohnishi et al. |
| 7,652,468 | B2 | 1/2010 | Kruger et al. |
| 7,652,578 | B2 | 1/2010 | Braun et al. |
| 7,657,300 | B2 | 2/2010 | Hunter et al. |
| 7,659,912 | B2 | 2/2010 | Akimoto et al. |
| 7,660,623 | B2 | 2/2010 | Hunter et al. |
| 7,680,528 | B2 | 3/2010 | Pfister et al. |
| 7,684,849 | B2 | 3/2010 | Wright et al. |
| 7,686,767 | B2 | 3/2010 | Maschke |
| 7,688,064 | B2 | 3/2010 | Shalgi et al. |
| 7,696,899 | B2 | 4/2010 | Immerz et al. |

| | | | |
|---|---|---|---|
| 7,697,972 B2 | 4/2010 | Verard et al. | |
| 7,697,973 B2 | 4/2010 | Strommer et al. | |
| 7,697,974 B2 | 4/2010 | Jenkins et al. | |
| 7,720,517 B2 | 5/2010 | Drysen | |
| 7,722,565 B2 | 5/2010 | Wood et al. | |
| 7,725,154 B2 | 5/2010 | Beck et al. | |
| 7,725,164 B2 | 5/2010 | Suurmond et al. | |
| 7,727,269 B2 | 6/2010 | Abraham-Fuchs et al. | |
| 7,729,742 B2 | 6/2010 | Govari | |
| 7,744,605 B2 | 6/2010 | Vilsmeier et al. | |
| 7,747,307 B2 | 6/2010 | Wright et al. | |
| 7,751,865 B2 | 7/2010 | Jascob et al. | |
| 7,782,189 B2 | 8/2010 | Spoonhower et al. | |
| 7,784,468 B2 | 8/2010 | Fabian et al. | |
| 7,831,076 B2 | 11/2010 | Altmann et al. | |
| 7,912,662 B2 | 3/2011 | Zuhars et al. | |
| 7,969,143 B2 | 6/2011 | Gilboa | |
| 2001/0007918 A1 | 7/2001 | Vilsmeier et al. | |
| 2001/0031919 A1 | 10/2001 | Strommer et al. | |
| 2001/0034530 A1 | 10/2001 | Malackowski et al. | |
| 2001/0036245 A1 | 11/2001 | Kienzle, III et al. | |
| 2001/0038705 A1 | 11/2001 | Rubbert et al. | |
| 2002/0022837 A1 | 2/2002 | Mazzocchi et al. | |
| 2002/0045916 A1 | 4/2002 | Gray et al. | |
| 2002/0045919 A1 | 4/2002 | Johansson-Ruden et al. | |
| 2002/0065461 A1 | 5/2002 | Cosman | |
| 2002/0082498 A1 | 6/2002 | Wendt et al. | |
| 2002/0095081 A1 | 7/2002 | Vilsmeier | |
| 2002/0128565 A1 | 9/2002 | Rudy | |
| 2002/0137014 A1 | 9/2002 | Anderson et al. | |
| 2002/0143324 A1 | 10/2002 | Edwards | |
| 2002/0165448 A1 | 11/2002 | Ben-Haim et al. | |
| 2002/0173689 A1 | 11/2002 | Kaplan | |
| 2002/0193686 A1 | 12/2002 | Gilboa | |
| 2003/0018251 A1 | 1/2003 | Solomon | |
| 2003/0074011 A1 | 4/2003 | Gilboa et al. | |
| 2003/0086599 A1 | 5/2003 | Armato, III et al. | |
| 2003/0099390 A1 | 5/2003 | Zeng et al. | |
| 2003/0142753 A1 | 7/2003 | Gunday | |
| 2003/0144658 A1 | 7/2003 | Schwartz et al. | |
| 2003/0160721 A1 | 8/2003 | Gilboa et al. | |
| 2003/0216639 A1 | 11/2003 | Gilboa et al. | |
| 2004/0000249 A1 | 1/2004 | Avetisian | |
| 2004/0006268 A1 | 1/2004 | Gilboa et al. | |
| 2004/0015049 A1 | 1/2004 | Zaar | |
| 2004/0019350 A1 | 1/2004 | O'Brien et al. | |
| 2004/0024309 A1 | 2/2004 | Ferre et al. | |
| 2004/0086161 A1 | 5/2004 | Sivaramakrishna et al. | |
| 2004/0097804 A1 | 5/2004 | Sobe | |
| 2004/0122310 A1 | 6/2004 | Lim | |
| 2004/0138548 A1 | 7/2004 | Strommer et al. | |
| 2004/0143317 A1 | 7/2004 | Stinson et al. | |
| 2004/0169509 A1 | 9/2004 | Czipott et al. | |
| 2004/0215181 A1 | 10/2004 | Christopherson et al. | |
| 2004/0249267 A1* | 12/2004 | Gilboa | 600/424 |
| 2004/0254454 A1 | 12/2004 | Kockro | |
| 2005/0018885 A1 | 1/2005 | Chen et al. | |
| 2005/0027193 A1 | 2/2005 | Mitschke et al. | |
| 2005/0033149 A1 | 2/2005 | Strommer et al. | |
| 2005/0059890 A1 | 3/2005 | Deal et al. | |
| 2005/0085715 A1 | 4/2005 | Dukesher et al. | |
| 2005/0090818 A1 | 4/2005 | Pike, Jr. et al. | |
| 2005/0107688 A1 | 5/2005 | Strommer | |
| 2005/0119527 A1 | 6/2005 | Banik et al. | |
| 2005/0182295 A1 | 8/2005 | Soper et al. | |
| 2005/0197566 A1 | 9/2005 | Strommer et al. | |
| 2005/0272971 A1 | 12/2005 | Ohnishi et al. | |
| 2006/0015126 A1 | 1/2006 | Sher | |
| 2006/0058647 A1 | 3/2006 | Strommer et al. | |
| 2006/0064006 A1 | 3/2006 | Strommer et al. | |
| 2006/0079759 A1 | 4/2006 | Vaillant et al. | |
| 2006/0116575 A1 | 6/2006 | Willis | |
| 2006/0149134 A1 | 7/2006 | Soper et al. | |
| 2006/0241396 A1 | 10/2006 | Fabian et al. | |
| 2006/0241399 A1 | 10/2006 | Fabian | |
| 2007/0163597 A1 | 7/2007 | Mikkaichi et al. | |
| 2007/0167714 A1 | 7/2007 | Kiraly et al. | |
| 2007/0167738 A1 | 7/2007 | Timinger et al. | |
| 2007/0167743 A1 | 7/2007 | Honda et al. | |
| 2007/0167804 A1 | 7/2007 | Park et al. | |
| 2007/0167806 A1 | 7/2007 | Wood et al. | |
| 2007/0225553 A1 | 9/2007 | Shahidi | |
| 2007/0232898 A1 | 10/2007 | Huynh et al. | |
| 2007/0265639 A1 | 11/2007 | Danek et al. | |
| 2007/0287901 A1 | 12/2007 | Strommer et al. | |
| 2008/0008367 A1 | 1/2008 | Franaszek et al. | |
| 2008/0008368 A1 | 1/2008 | Matsumoto | |
| 2008/0018468 A1 | 1/2008 | Volpi et al. | |
| 2008/0033452 A1 | 2/2008 | Vetter et al. | |
| 2008/0086051 A1 | 4/2008 | Voegele | |
| 2008/0097154 A1 | 4/2008 | Makower et al. | |
| 2008/0097187 A1 | 4/2008 | Gielen et al. | |
| 2008/0118135 A1* | 5/2008 | Averbuch et al. | 382/131 |
| 2008/0132909 A1 | 6/2008 | Jascob et al. | |
| 2008/0132911 A1 | 6/2008 | Sobe | |
| 2008/0139886 A1 | 6/2008 | Tatsuyama | |
| 2008/0139915 A1 | 6/2008 | Dolan et al. | |
| 2008/0144909 A1 | 6/2008 | Wiemker et al. | |
| 2008/0147000 A1 | 6/2008 | Seibel et al. | |
| 2008/0154172 A1 | 6/2008 | Mauch | |
| 2008/0157755 A1 | 7/2008 | Kruger et al. | |
| 2008/0161682 A1 | 7/2008 | Kendrick et al. | |
| 2008/0162074 A1 | 7/2008 | Schneider | |
| 2008/0183071 A1 | 7/2008 | Strommer et al. | |
| 2008/0188749 A1 | 8/2008 | Rasche et al. | |
| 2008/0247622 A1 | 10/2008 | Aylward et al. | |
| 2009/0082665 A1 | 3/2009 | Anderson | |
| 2009/0182224 A1 | 7/2009 | Shmarak et al. | |
| 2009/0189820 A1 | 7/2009 | Saito et al. | |
| 2009/0318797 A1 | 12/2009 | Hadani | |
| 2010/0016658 A1 | 1/2010 | Zou et al. | |
| 2011/0085720 A1* | 4/2011 | Averbuch | 382/131 |

FOREIGN PATENT DOCUMENTS

| | | |
|---|---|---|
| DE | 35 08 730 A1 | 9/1986 |
| DE | 35 20 782 A1 | 12/1986 |
| DE | 37 17 871 A1 | 12/1988 |
| DE | 38 31 278 A1 | 3/1989 |
| DE | 38 38 011 A1 | 7/1989 |
| DE | 42 13 426 A1 | 10/1992 |
| DE | 42 25 112 C1 | 12/1993 |
| DE | 42 33 978 C1 | 4/1994 |
| DE | 197 15 202 A1 | 10/1998 |
| DE | 197 51 761 A1 | 10/1998 |
| DE | 198 32 296 A1 | 2/1999 |
| DE | 197 47 427 A1 | 5/1999 |
| DE | 100 85 137 T1 | 11/2002 |
| EP | 0 062 941 A1 | 10/1982 |
| EP | 0 119 660 A1 | 9/1984 |
| EP | 0 155 857 A2 | 9/1985 |
| EP | 0 319 844 A1 | 6/1989 |
| EP | 0 326 768 A2 | 8/1989 |
| EP | 0 350 996 A1 | 1/1990 |
| EP | 0 419 729 A1 | 4/1991 |
| EP | 0 427 358 A1 | 5/1991 |
| EP | 0 456 103 A2 | 11/1991 |
| EP | 0 600 610 A2 | 6/1993 |
| EP | 0 581 704 A1 | 2/1994 |
| EP | 0 651 968 A1 | 5/1995 |
| EP | 0 796 633 A1 | 9/1997 |
| EP | 0 908 146 A2 | 10/1997 |
| EP | 0 930 046 A2 | 11/1997 |
| EP | 0 829 229 A1 | 3/1998 |
| EP | 0 655 138 B1 | 4/1998 |
| EP | 0 857 461 A2 | 8/1998 |
| EP | 0 894 473 A2 | 2/1999 |
| EP | 0 922 966 A2 | 6/1999 |
| EP | 1 078 644 A1 | 8/1999 |
| EP | 2 096 523 A1 | 9/2009 |
| FR | 2 417 970 A1 | 9/1979 |
| FR | 2 618 211 A1 | 1/1989 |
| GB | 2 094 590 A | 9/1982 |
| GB | 2 164 856 A | 4/1986 |
| GB | 2 197 078 A | 5/1988 |
| JP | 63-240851 A | 10/1988 |
| JP | 03-025752 B | 4/1991 |
| JP | 03-267054 A | 11/1991 |
| JP | 06-194639 A | 7/1994 |

| | | | |
|---|---|---|---|
| JP | 07-159378 A | 6/1995 | |
| JP | 08-233601 A | 9/1996 | |
| JP | 08-299305 A | 11/1996 | |
| WO | WO 88/09151 A1 | 12/1988 | |
| WO | WO 89/05123 A1 | 6/1989 | |
| WO | WO 90/05494 A1 | 5/1990 | |
| WO | WO 91/03982 A1 | 4/1991 | |
| WO | WO 91/04711 A1 | 4/1991 | |
| WO | WO 91/07726 A1 | 5/1991 | |
| WO | WO 92/03090 A1 | 3/1992 | |
| WO | WO 92/06645 A1 | 4/1992 | |
| WO | WO 94/04938 A1 | 3/1994 | |
| WO | WO 94/23647 A1 | 10/1994 | |
| WO | WO 94/24933 A1 | 11/1994 | |
| WO | WO 95/07055 A1 | 3/1995 | |
| WO | WO 95/09562 A1 | 4/1995 | |
| WO | WO96/05768 A1 | 2/1996 | |
| WO | WO 96/11624 A1 | 4/1996 | |
| WO | WO96/25882 A1 | 8/1996 | |
| WO | WO 96/32059 A1 | 10/1996 | |
| WO | WO 96/41119 A1 | 12/1996 | |
| WO | WO 97/00011 A1 | 1/1997 | |
| WO | WO 97/00054 A1 | 1/1997 | |
| WO | WO 97/00058 A1 | 1/1997 | |
| WO | WO 97/00059 A1 | 1/1997 | |
| WO | WO 97/00308 A1 | 1/1997 | |
| WO | WO 97/02650 A1 | 1/1997 | |
| WO | WO 97/24983 A2 | 7/1997 | |
| WO | WO 97/25101 A2 | 7/1997 | |
| WO | WO 97/29682 A1 | 8/1997 | |
| WO | WO 97/29684 A1 | 8/1997 | |
| WO | WO 97/29685 A1 | 8/1997 | |
| WO | WO 97/29701 A1 | 8/1997 | |
| WO | WO 97/29709 A1 | 8/1997 | |
| WO | WO 97/36143 A1 | 10/1997 | |
| WO | WO 97/36192 A1 | 10/1997 | |
| WO | WO 97/42517 A1 | 11/1997 | |
| WO | WO 97/44089 A1 | 11/1997 | |
| WO | WO 97/49453 A1 | 12/1997 | |
| WO | WO 98/00034 A2 | 1/1998 | |
| WO | WO 98/08554 A1 | 3/1998 | |
| WO | WO 98/11840 A1 | 3/1998 | |
| WO | WO 98/29032 A1 | 7/1998 | |
| WO | WO 98/35720 A2 | 8/1998 | |
| WO | WO 98/38908 A1 | 9/1998 | |
| WO | WO 98/48722 A1 | 11/1998 | |
| WO | WO 99/15097 A1 | 4/1999 | |
| WO | WO 99/16350 A1 | 4/1999 | |
| WO | WO 99/21498 A1 | 5/1999 | |
| WO | WO 99/23956 A1 | 5/1999 | |
| WO | WO 99/26549 A1 | 6/1999 | |
| WO | WO 99/26826 A2 | 6/1999 | |
| WO | WO 99/27839 A1 | 6/1999 | |
| WO | WO 99/29253 A1 | 6/1999 | |
| WO | WO 99/30777 A1 | 6/1999 | |
| WO | WO 99/32033 A1 | 7/1999 | |
| WO | WO 99/33406 A1 | 7/1999 | |
| WO | WO 99/37208 A1 | 7/1999 | |
| WO | WO 99/38449 A1 | 8/1999 | |
| WO | WO 99/52094 A1 | 10/1999 | |
| WO | WO 99/55415 A1 | 11/1999 | |
| WO | WO 99/60939 A1 | 12/1999 | |
| WO | WO 00/06701 A1 | 2/2000 | |
| WO | WO 00/10456 A1 | 3/2000 | |
| WO | WO 00/16684 A1 | 3/2000 | |
| WO | WO 00/35531 A1 | 6/2000 | |
| WO | WO 01/06917 A1 | 2/2001 | |
| WO | WO 01/12057 A1 | 2/2001 | |
| WO | WO 01/30437 A1 | 5/2001 | |
| WO | WO 01/67035 A1 | 9/2001 | |
| WO | WO 01/87136 A2 | 11/2001 | |
| WO | WO 01/91842 A1 | 12/2001 | |
| WO | WO 02/064011 A2 | 8/2002 | |
| WO | WO 02/070047 A1 | 9/2002 | |
| WO | WO 03/086498 A2 | 10/2003 | |
| WO | WO 2004/023986 A1 | 3/2004 | |
| WO | WO 2006/116597 A2 | 11/2006 | |

OTHER PUBLICATIONS

United States Patent and Trademark Office, Final Office Action mailed Apr. 23, 2012 in U.S. Appl. No. 12/170,385, 15 pages.
United States Patent and Trademark Office, Office Action mailed Mar. 29, 2012 in U.S. Appl. No. 12/723,577, 11 pages.
United States Patent and Trademark Office, Notice of Allowance mailed Mar. 22, 2012 in U.S. Appl. No. 12/466,238, 11 pages.
United States Patent and Trademark Office, Notice of Allowance mailed Mar. 19, 2012 in U.S. Appl. No. 12/478,573, 12 pages.
United States Patent and Trademark Office, Office Action mailed Mar. 5, 2012 in U.S. Appl. No. 11/568,260, 12 pages.
United States Patent and Trademark Office, Final Office Action mailed Dec. 15, 2011 in U.S. Appl. No. 12/369,466, 11 pages.
United States Patent and Trademark Office, Office Action mailed Dec. 15, 2011 in U.S. Appl. No. 12/170,385, 19 pages.
United States Patent and Trademark Office, Final Office Action mailed Nov. 22, 2011 in U.S. Appl. No. 12/417,381, 21 pages.
United States Patent and Trademark Office, Office Action mailed Nov. 18, 2011 in U.S. Appl. No. 12/476,976, 6 pages.
United States Patent and Trademark Office, Final Office Action mailed Nov. 4, 2011 in U.S. Appl. No. 11/393,537, 22 pages.
United States Patent and Trademark Office, Office Action mailed Nov. 2, 2011 in U.S. Appl. No. 12/478,573, 11 pages.
European Patent Office, Examination Report dated Sep. 30, 2011 in European Patent Application No. EP05737664, 5 pages.
WIPO, U.S. International Preliminary Examining Authority, International Preliminary Report on Patentability mailed Sep. 29, 2011 in International Patent Application No. PCT/US2010/027544, 5 pages.
United States Patent and Trademark Office, Final Office Action mailed Sep. 23, 2011 in U.S. Appl. No. 12/723,577, 12 pages.
European Patent Office, Examination Report dated Sep. 9, 2011 in European Patent Application No. EP0916050, 6 pages.
United States Patent and Trademark Office, Office Action mailed Sep. 7, 2011 in U.S. Appl. No. 12/466,238, 14 pages.
European Patent Office, Extended European Search Report dated Sep. 6, 2011 in European Patent Application No. EP03719056, 6 pages.
European Patent Office, Extended European Search Report dated Sep. 6, 2011 in European Patent Application No. EP1117466, 6 pages.
United States Patent and Trademark Office, Final Office Action mailed Jul. 27, 2011 in U.S. Appl. No. 12/723,577, 12 pages.
WIPO, U.S. International Search Authority, International Search Report and Written Opinion mailed Jul. 12, 2006 in International Patent Application No. PCT/IB2011/000243, 7 pages.
United States Patent and Trademark Office, Office Action mailed Apr. 29, 2011 in U.S. Appl. No. 12/417,381, 12 pages.
United States Patent and Trademark Office, Notice of Allowance mailed Apr. 6, 2011 in U.S. Appl. No. 11/765,330, 9 pages.
United States Patent and Trademark Office, Office Action mailed Apr. 1, 2011 in U.S. Appl. No. 11/393,537, 21 pages.
United States Patent and Trademark Office, Office Action mailed Mar. 31, 2011 in U.S. Appl. No. 12/490,237, 7 pages.
United States Patent and Trademark Office, Office Action mailed Mar. 18, 2011 in U.S. Appl. No. 12/369,466, 13 pages.
United States Patent and Trademark Office, Office Action mailed Feb. 16, 2011 in U.S. Appl. No. 12/723,577, 8 pages.
European Patent Office, Extended European Search Report dated Jan. 24, 2011 in European Patent Application No. EP10182338, 8 pages.
United States Patent and Trademark Office, Final Office Action mailed Dec. 17, 2010 in U.S. Appl. No. 12/723,577, 8 pages.
United States Patent and Trademark Office, Final Office Action mailed Dec. 10, 2010 in U.S. Appl. No. 12/503,045, 11 pages.
WIPO, U.S. International Preliminary Examining Authority, International Preliminary Report on Patentability mailed Dec. 6, 2010 in International Patent Application No. PCT/IL2009/000569, 6 pages.
European Patent Office, Extended European Search Report dated Nov. 15, 2010 in European Patent Application No. EP10159373, 12 pages.
United States Patent and Trademark Office, Office Action mailed Nov. 15, 2010 in U.S. Appl. No. 12/490,237, 8 pages.

European Patent Office, Examination Report dated Oct. 26, 2010 in European Patent Application No. EP05737664, 3 pages.
United States Patent and Trademark Office, Office Action mailed Oct. 22, 2010 in U.S. Appl. No. 12/723,577, 7 pages.
European Patent Office, Examination Report dated Oct. 20, 2010 in European Patent Application No. EP06100566, 6 pages.
United States Patent and Trademark Office, Office Action mailed Oct. 18, 2010 in U.S. Appl. No. 11/765,330, 35 pages.
European Patent Office, Examination Report dated Aug. 11, 2010 in European Patent Application No. EP03719056, 4 pages.
United States Patent and Trademark Office, Office Action mailed May 19, 2010 in U.S. Appl. No. 12/503,045, 12 pages.
WIPO, U.S. International Search Authority, International Search Report mailed May 17, 2010 in International Patent Application No. PCT/US2010/027544, 2 pages.
WIPO, U.S. International Search Authority, Written Opinion mailed May 17, 2010 in International Patent Application No. PCT/US2010/027544, 3 pages.
WIPO, U.S. International Preliminary Examining Authority, International Preliminary Report on Patentability mailed May 10, 2010 in International Patent Application No. PCT/192009/005167, 5 pages.
European Patent Office, Examination Report dated Mar. 30, 2010 in European Patent Application No. EP05737664, 5 pages.
European Patent Office, Examination Report dated Feb. 18, 2010 in European Patent Application No. EP0916050, 9 pages.
European Patent Office, Supplementary European Search Report dated Feb. 2, 2010 in European Patent Application No. EP03719056, 3 pages.
United States Patent and Trademark Office, Office Action mailed Dec. 31, 2009 in U.S. Appl. No. 11/427,353, 9 pages.
European Patent Office, Supplementary European Search Report dated Nov. 6, 2009 in European Patent Application No. EP05737664, 7 pages.
WIPO, U.S. International Search Authority, International Search Report and Written Opinion mailed Oct. 26, 2009 in International Patent Application No. PCT/IB2009/005609, 11 pages.
WIPO, U.S. International Search Authority, International Search Report and Written Opinion mailed Sep. 25, 2009 in International Patent Application No. PCT/IB2009/005167, 5 pages.
WIPO, U.S. International Search Authority, International Search Report and Written Opinion mailed Sep. 24, 2009 in International Patent Application No. PCT/IL2009/000569, 7 pages.
WIPO, U.S. International Search Authority, International Search Report and Written Opinion mailed Sep. 22, 2009 in International Patent Application No. PCT/IL2009/000553, 7 pages.
United States Patent and Trademark Office, Final Office Action mailed Aug. 7, 2009 in U.S. Appl. No. 11/427,353, 7 pages.
Japan Patent Office, Official Action dated Jul. 31, 2009 in Japanese Patent Application Serial No. 2005-005767, 6 pages.
European Patent Office, Examination Report dated Jul. 14, 2009 in European Patent Application No. EP03719056, 6 pages.
WIPO, IB International Search Authority, International Search Report mailed Jul. 14, 2009 in International Patent Application No. PCT/IB2009/000238, 1 pages.
Japan Patent Office, Official Action dated Jul. 3, 2009 in Japanese Patent Application Serial No. JP2005-001768, 6 pages.
United States Patent and Trademark Office, Office Action mailed Jun. 24, 2009 in U.S. Appl. No. 10/129,365, 5 pages.
European Patent Office, Extended European Search Report dated Jun. 22, 2009 in European Patent Application No. EP0916050, 8 pages.
Japan Patent Office, Official Action dated Jun. 19, 2009 in Japanese Patent Application Serial No. JP2005-001769, 2 pages.
European Patent Office, Extended European Search Report dated Feb. 27, 2009 in European Patent Application No. ep03719056, 6 pages.
United States Patent and Trademark Office, Notice of Allowance mailed Feb. 25, 2009 in U.S. Appl. No. 10/408,123, 8 pages.
European Patent Office, Examination Report dated Feb. 11, 2009 in European Patent Application No. EP01925833, 4 pages.
United States Patent and Trademark Office, Final Office Action mailed Jan. 23, 2009 in U.S. Appl. No. 10/169,186, 9 pages.
United States Patent and Trademark Office, Office Action mailed Jan. 22, 2009 in U.S. Appl. No. 11/427,353, 8 pages.
United States Patent and Trademark Office, Final Office Action mailed Jan. 14, 2009 in U.S. Appl. No. 10/190,847, 12 pages.
United States Patent and Trademark Office, Office Action mailed Nov. 13, 2008 in U.S. Appl. No. 10/258,124, 13 pages.
WIPO, U.S. International Search Authority, International Search Report and Written Opinion mailed Nov. 13, 2008 in International Patent Application No. PCT/US07/004567, 8 pages.
United States Patent and Trademark Office, Office Action mailed Nov. 4, 2008 in U.S. Appl. No. 10/129,365, 7 pages.
European Patent Office, Office Action mailed Sep. 3, 2008 in European Patent Application No. 98 204 113.9, 2 pages.
European Patent Office, Extended European Search Report dated Aug. 3, 2008 in European Patent Application No. EP8158218, 2 pages.
United States Patent and Trademark Office, Final Office Action mailed Jun. 24, 2008 in U.S. Appl. No. 10/258,124, 11 pages.
United States Patent and Trademark Office, Office Action mailed May 15, 2008 in U.S. Appl. No. 10/190,847, 13 pages.
United States Patent and Trademark Office, Office Action mailed May 15, 2008 in U.S. Appl. No. 10/169,186, 9 pages.
United States Patent and Trademark Office, Office Action mailed May 13, 2008 in U.S. Appl. No. 10/408,123, 6 pages.
Higgins, W.E. et al., "3D CT-Video Fusion for Image-Guided Bronchoscopy," *Comput Med Imaging Graph* Apr. 2008; 32(3):159-73, 30 pages.
European Patent Office, Examination Report dated Feb. 27, 2008 in European Patent Application No. EP99946419, 7 pages.
United States Patent and Trademark Office, Final Office Action mailed Dec. 31, 2007 in U.S. Appl. No. 10/129,365, 7 pages.
European Patent Office, Supplementary European Search Report dated Nov. 28, 2007 in European Patent Application No. EP01925833, 3 pages.
United States Patent and Trademark Office, Final Office Action mailed Oct. 11, 2007 in U.S. Appl. No. 10/190,847, 13 pages.
United States Patent and Trademark Office, Final Office Action mailed Oct. 5, 2007 in U.S. Appl. No. 10/169,186, 9 pages.
European Patent Office, Office Action mailed Aug. 31, 2007 in European Patent Application No. 98 204 113.9, 3 pages.
United States Patent and Trademark Office, Office Action mailed Jul. 27, 2007 in U.S. Appl. No. 10/408,123, 6 pages.
United States Patent and Trademark Office, Office Action mailed Jul. 11, 2007 in U.S. Appl. No. 10/258,124, 10 pages.
European Patent Office, Examination Report dated May 24, 2007 in European Patent Application No. EP06100566, 3 pages.
United States Patent and Trademark Office, Office Action mailed Mar. 26, 2007 in U.S. Appl. No. 10/190,847, 5 pages.
United States Patent and Trademark Office, Office Action mailed Dec. 4, 2006 in U.S. Appl. No. 10/169,186, 9 pages.
United States Patent and Trademark Office, Final Office Action mailed Nov. 29, 2006 in U.S. Appl. No. 10/258,124, 11 pages.
United States Patent and Trademark Office, Notice of Allowance mailed Oct. 6, 2006 in U.S. Appl. No. 10/491,099, 9 pages.
United States Patent and Trademark Office, Office Action mailed Sep. 21, 2006 in U.S. Appl. No. 10/408,123, 9 pages.
Palágyi, K. et al., "Quantitative analysis of pulmonary airway tree structures," *Computers in Biology and Medicine* 36 (2006) 974-996, Sep. 2006, 23 pages.
European Patent Office, Examination Report dated Aug. 24, 2006 in European Patent Application No. EP99946419, 6 pages.
United States Patent and Trademark Office, Office Action mailed Aug. 4, 2006 in U.S. Appl. No. 10/190,847, 7 pages.
WIPO, U.S. International Preliminary Examining Authority, International Preliminary Report on Patentability mailed Jul. 19, 2006 in International Patent Application No. PCT/IL2005/000724, 4 pages.
United States Patent and Trademark Office, Final Office Action mailed Jul. 14, 2006 in U.S. Appl. No. 10/129,365, 8 pages.
WIPO, U.S. International Search Authority, International Search Report mailed Mar. 30, 2006 in International Patent Application No. PCT/IL2005/000452, 1 page.
European Patent Office, Examination Report dated Mar. 17, 2006 in European Patent Application No. 98 204 133, 3 pages.

WIPO, U.S. International Search Authority, International Search Report mailed Mar. 14, 2006 in International Patent Application No. PCT/IL2005/000724, 1 page.
European Patent Office, Examination Report dated Mar. 9, 2006 in European Patent Application No. EP06100566, 6 pages.
United States Patent and Trademark Office, Office Action mailed Dec. 30, 2005 in U.S. Appl. No. 10/491,099, 15 pages.
United States Patent and Trademark Office, Office Action mailed Dec. 13, 2005 in U.S. Appl. No. 10/129,365, 7 pages.
United States Patent and Trademark Office, Office Action mailed Dec. 1, 2005 in U.S. Appl. No. 10/258,124, 12 pages.
European Patent Office, Examination Report dated Aug. 8, 2005 in European Patent Application No. 98 204 133, 3 pages.
United States Patent and Trademark Office, Office Action mailed Apr. 22, 2005 in U.S. Appl. No. 10/491,099, 5 pages.
European Patent Office, Examination Report dated Apr. 15, 2005 in European Patent Application No. EP99946419, 6 pages.
United States Patent and Trademark Office, Final Office Action mailed Mar. 29, 2005 in U.S. Appl. No. 09/959,837, 4 pages.
United States Patent and Trademark Office, Office Action mailed Feb. 24, 2005 in U.S. Appl. No. 09/879,107, 6 pages.
United States Patent and Trademark Office, Notice of Allowance mailed Jan. 3, 2005 in U.S. Appl. No. 10/137,415, 10 pages.
United States Patent and Trademark Office, Notice of Allowance mailed Jan. 3, 2005 in U.S. Appl. No. 09/879,109, 6 pages.
United States Patent and Trademark Office, Office Action mailed Nov. 26, 2004 in U.S. Appl. No. 09/959,837, 8 pages.
Shmarak, Itzhak et al., U.S. Appl. No. 10/986,567, filed Nov. 10, 2004 (abandoned, unpublished), 84 pages.
European Patent Office, Examination Report dated Aug. 25, 2004 in European Patent Application No. EP98204113, 4 pages.
United States Patent and Trademark Office, Office Action mailed Jul. 1, 2004 in U.S. Appl. No. 10/137,415, 14 pages.
United States Patent and Trademark Office, Office Action mailed Jan. 21, 2004 in U.S. Appl. No. 09/959,837, 8 pages.
United States Patent and Trademark Office, Office Action mailed Nov. 13, 2002 in U.S. Appl. No. 09/463,177, 5 pages.
United States Patent and Trademark Office, Office Action mailed Sep. 6, 2002 in U.S. Appl. No. 09/463,177, 8 pages.
WIPO, U.S. International Preliminary Examining Authority, International Preliminary Examination Report mailed Aug. 7, 2002 in International Patent Application No. PCT/US1999/026826, 4 pages.
WIPO, U.S. International Search Authority, International Search Report mailed Jul. 31, 2002 in International Patent Application No. PCT/US2002/013317, 1 page.
United States Patent and Trademark Office, Notice of Allowance mailed Mar. 26, 2002 in U.S. Appl. No. 09/860,484, 6 pages.
WIPO, U.S. International Search Authority, International Search Report mailed Feb. 13, 2002 in International Patent Application No. PCT/IL2001/000415, 2 pages.
United States Patent and Trademark Office, Office Action mailed Jan. 16, 2002 in U.S. Appl. No. 09/860,484, 7 pages.
WIPO, U.S. International Search Authority, International Search Report mailed Jan. 3, 2002 in International Patent Application No. PCT/IL2001/000363, 2 pages.
WIPO, U.S. International Search Authority, International Search Report mailed Nov. 16, 2001 in International Patent Application No. PCT/IL2000/000735, 1 page.
WIPO, U.S. International Search Authority, International Search Report mailed Aug. 14, 2001 in International Patent Application No. PCT/IL2001/000224, 3 pages.
WIPO, U.S. International Preliminary Examining Authority, International Preliminary Report on Patentability mailed Aug. 9, 2001 in International Patent Application No. PCT/IS2000/026322, 4 pages.
WIPO, U.S. International Search Authority, International Search Report mailed Jun. 27, 2001 in International Patent Application No. PCT/IL2001/000024, 7 pages.
WIPO, U.S. International Search Authority, International Search Report mailed Feb. 23, 2001 in International Patent Application No. PCT/IL2000/00537, 3 pages.
WIPO, U.S. International Search Authority, International Search Report mailed Nov. 28, 2000 in International Patent Application No. PCT/US2000/026322, 1 page.
WIPO, U.S. International Search Authority, International Search Report mailed Nov. 27, 2000 in International Patent Application No. PCT/US2000/021669, 1 page.
Ost et al., "Evaluation and Management of the Solitary Pulmonary Nodule," *Am J Respir Crit Care Med* vol. 162, pp. 782-787, Sep. 2000, 5 pages.
European Patent Office, Supplementary European Search Report dated May 11, 2000 in European Patent Application No. 98 204 133, 3 pages.
WIPO, U.S. International Search Authority, International Search Report mailed Mar. 31, 2000 in International Patent Application No. PCT/US1999/026826, 1 page.
WIPO, U.S. International Search Authority, International Search Report mailed Feb. 23, 2000 in International Patent Application No. PCT/US1999/026095, 1 page.
WIPO, U.S. International Search Authority, International Search Report mailed Feb. 10, 2000 in International Patent Application No. PCT/IL1999/000371, 1 page.
U.S. Appl. No. 09/463,176, filed Jan. 21, 2000 (now U.S. Patent 6,711,429 issued Mar. 23, 2004), 107 pages.
U.S. Appl. No. 09/463,177, filed Jan. 21, 2000 (now U.S. Patent 6,593,884 issued Jul. 15, 2003), 66 pages.
Herman, G.T. et al., *Discrete Tomography*, Birkhauser, 1999, 3 pages.
WIPO, U.S. International Search Authority, International Search Report mailed Sep. 3, 1997 in International Patent Application No. PCT/IL1997/000054, 1 page.
Ramm, G. et al., *The Radon Transform and Local Tomography*, CRC Press, 1996, 10 pages.
Natterer, F., *The Mathematics of Computerized Tomography*, Wiley, 1989, 4 pages.
Herman, G.T. et al., *Basic Methods of Tomography and Inverse Problems*, Hildger, 1987, 5 pages.
Breyer, B. et al., "Ultrasonically marked catheter—a method for positive echographic catheter position identification," *Medical & Biological Engineering & Computing*, May 1984, 22(3)268-271, 4 pages.

* cited by examiner

FEATURE-BASED REGISTRATION METHOD

RELATED APPLICATIONS

This application claims priority to U.S. Provisional Application Ser. No. 61/058,470 filed Jun. 3, 2008 entitled Feature-Based Registration Method, which is hereby incorporated herein by reference.

BACKGROUND OF THE INVENTION

Breakthrough technology has emerged which allows the navigation of a catheter tip through a tortuous channel, such as those found in the pulmonary system, to a predetermined target. This technology compares the real-time movement of a sensor against a three-dimensional digital map of the targeted area of the body (for purposes of explanation, the pulmonary airways of the lungs will be used hereinafter, though one skilled in the art will realize the present invention could be used in any body cavity or system: circulatory, digestive, pulmonary, to name a few).

Such technology is described in U.S. Pat. Nos. 6,188,355; 6,226,543; 6,558,333; 6,574,498; 6,593,884; 6,615,155; 6,702,780; 6,711,429; 6,833,814; 6,974,788; and 6,996,430, all to Gilboa or Gilboa et al.; and U.S. Published Applications Pub. Nos. 2002/0193686; 2003/0074011; 2003/0216639; 2004/0249267 to either Gilboa or Gilboa et al. All of these references are incorporated herein in their entireties.

Using this technology begins with recording a plurality of images of the applicable portion of the patient, for example, the lungs. These images are often recorded using CT technology. CT images are two-dimensional slices of a portion of the patient. After taking several, parallel images, the images may be "assembled" by a computer to form a three-dimensional model, or "CT volume" of the lungs.

The CT volume is used during the procedure as a map to the target. The physician navigates a steerable probe that has a trackable sensor at its distal tip. The sensor provides the system with a real-time image of its location. However, because the image of the sensor location appears as a vector on the screen, the image has no context without superimposing the CT volume over the image provided by the sensor. The act of superimposing the CT volume and the sensor image is known as "registration."

There are various registration methods, some of which are described in the aforementioned references. For example, point registration involves selecting a plurality of points, typically identifiable anatomical landmarks, inside the lung from the CT volume and then using the sensor (with the help of an endoscope) and "clicking" on each of the corresponding landmarks in the lung. Clicking on the landmarks refers to activating a record feature on the sensor that signifies the registration point should be recorded. The recorded points are then aligned with the points in the CT volume, such that registration is achieved. This method works well for initial registration in the central area but as the sensor is navigated to the distal portions of the lungs, the registration becomes less accurate as the distal airways are smaller and move more with the breathing cycle.

Another example of a registration method is to record a segment of an airway and shape-match that segment to a corresponding segment in the CT volume. This method of registration suffers similar setbacks to the point registration method, though it can be used in more distal airways because an endoscope is not required. The registration should be conducted more than once to keep the registration updated. It may be inconvenient or otherwise undesirable to require additional registration steps from a physician. Additionally, this method requires that a good image exists in the CT volume for any given airway occupied by the sensor. If for example, the CT scan resulted in an airway shadowed by a blood vessel, for example, the registration will suffer because the shape data on that airway is compromised.

An alternative registration method known as "Adaptive Navigation" was developed and described in U.S. Published Application 2008/0118135 to Averbuch et al., incorporated by reference herein in its entirety. This registration technique operates on the assumption that the sensor remains in the airways at all times. The position of the sensor is recorded as the sensor is advanced, thus providing a shaped historical path of where the sensor has been. This registration method requires the development of a computer-generated and automatically or manually segmented "Bronchial Tree" (BT). The shape of the historical path is matched to a corresponding shape in the BT.

Segmenting the BT involves converting the CT volume into a series of digitally-identified branches to develop, or "grow," a virtual model of the lungs. Automatic segmentation works well on the well-defined, larger airways and smaller airways that were imaged well in the CT scans. However, as the airways get smaller, the CT scan gets "noisier" and makes continued automatic segmentation inaccurate. Noise results from poor image quality, small airways, or airways that are shadowed by other features such as blood vessels. Noise can cause the automatic segmentation process to generate false branches and/or loops—airways that rejoin, an occurrence not found in the actual lungs.

It would be advantageous to provide a registration method that is automatic and continuous, and has an increased accuracy potential that is achieved without requiring any steps to be taken by a physician.

SUMMARY OF THE INVENTION

In view of the foregoing, one aspect of the present invention provides a feature-based registration method. When the CT scans are taken, the CT machine records each image as a plurality of pixels. When the various scans are assembled together to form a CT volume, voxels (volumetric pixels) appear and can be defined as volume elements, representing values on a regular grid in three dimensional space. Each of the voxels is assigned a number based on the tissue density Housefield number. This density value can be associated with gray level or color using well known window-leveling techniques.

One aspect of the present invention relates to the voxelization of the sensing volume of an electromagnetic field by digitizing it into voxels of a specific size compatible with the CT volume. Each voxel visited by the sensor can be assigned a value that correlates to the frequency with which that voxel is visited by the sensor. The densities of the voxels in the CT volume are adjusted according to these values, thereby creating clouds of voxels in the CT volume having varying densities. These voxels clouds or clusters thus match the interior anatomical features of the lungs.

Another aspect of the present invention is to provide a plurality of parameters that a particular voxel of the CT volume must meet before being considered as a candidate for matching to a corresponding voxel in the sensor sensing volume. For example, the voxel could be required to meet parameters such as: 1) falls within a particular density range, 2) falls within a predefined proximity from a currently accepted (registered) voxel, 3) fits within a specific template such as a group of continuous densities corresponding to air next to a plurality of densities corresponding to a blood vessel. This may be useful when it is known that, for example, a particular airway runs parallel to a pulmonary artery, so, for a given length, the airway voxels should be in specified proximity to pulmonary artery voxels.

One aspect of the present invention provides an iterative approach to registration. In other words, registration is continually updated and restarted, such that previous registration is being constantly discarded. This may be advantageous when, for example, navigating to a very distal portion of the lungs. Because the distal lungs move considerably with the breathing cycle, registration that occurred closer to the main carina may not be relevant to the distant areas. Additionally, using this iterative approach, the potential inaccuracy is not cumulative.

Another aspect of the present invention provides a continuous approach, as an alternative to the iterative approach, to registration. The continuous approach involves the step-by-step correction of the previously performed transformation of voxel-based cavity features to geometry-based structures and shapes.

Another aspect of the present invention is that, by using a voxel-based approach, registration is actually accomplished by comparing anatomical cavity features to cavity voxels, as opposed to anatomical shapes or locations to structure shapes or locations. An advantage of this approach is that air-filled cavities are of a predictable, constant density. Conversely, tissue, especially lung tissue, is of a variable, less predictable density. One skilled in the art will see that all of the technology described herein applies equally well to the vasculature of a patient. Blood-filled cavities, like air-filled cavities, are of a predictable, constant density.

DETAILED DESCRIPTION OF THE INVENTION

Generally, the present invention includes a system and method for registering a three-dimensional model of a body volume, such as a CT volume, to a real-time image of a sensor. This registration method compares anatomical cavity features to cavity voxels, as opposed to anatomical shapes or locations to structure shapes or locations.

Figure 1:
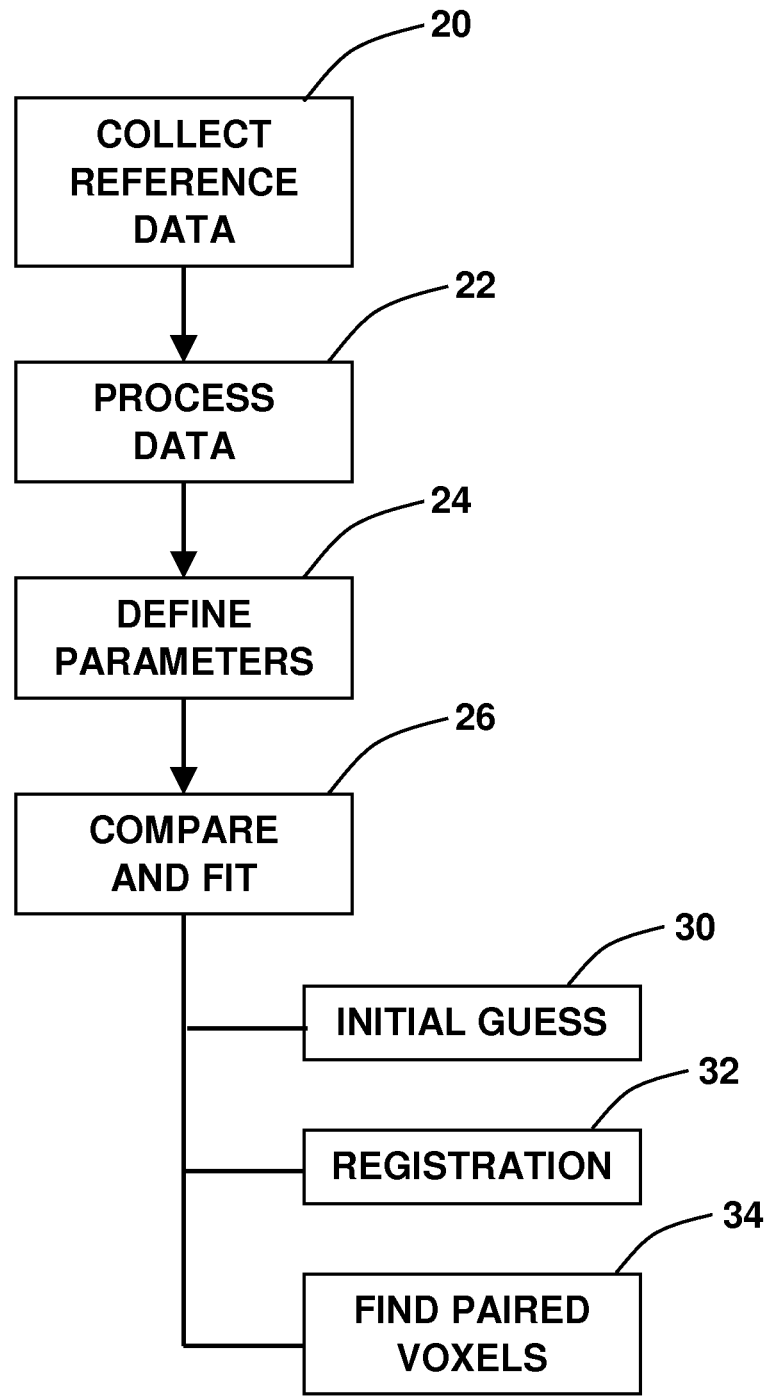
FIG. 1 is a flowchart of a method of the present invention.

Referring now to the flowchart of FIG. 1, it is shown that the method of the present invention begins at 20 with a collection of reference data. This step involves the acquisition of a plurality of CT scans, which are then assembled into a CT volume. During the procedure, the sensor is inserted into the lungs of the patient and a data stream is established between the sensor and a system processor.

At step 22, the data acquired is processed, which involves de-cluttering and digitization. Each of the voxels is assigned a number based on the tissue density Housefield number. This density value can be associated with gray level or color using well-known window-leveling techniques. The density is proportional to a probability that the sensor will occupy a given voxel. The data is also filtered as desired. For example, if the sensor is advanced slowly rather than quickly, it will necessarily result in higher densities as any one voxel is going to be occupied for a longer period of time while the sensor takes longer to pass through. Hence, an advancement rate may be noted and used to normalize the densities by speed, accordingly. After filtering, the voxels with higher densities are given higher weight in registration than voxels having lower densities.

At step 24 the desired parameters are defined. By way of example only, the voxel could be required to meet parameters such as: 1) falls within a particular density range, 2) falls within a predefined proximity from a currently accepted (registered) voxel, 3) fits within a specific template such as a group of continuous densities corresponding to air next to a plurality of densities corresponding to a blood vessel.

At 26, a compare and fit function is performed. This step includes multiple sub-steps, beginning with step 30. These steps are performed iteratively and repeatedly until the target is reached.

Step 30 involves an initial guess and is based on assumptions or known landmark techniques. For example, the main carina is relatively easy to match to the main carina of a BT.

At 32, the CT volume is registered to the sensor data using the initial guess and a difference between the two is calculated.

At 34, for each real voxel visited by the sensor, the registration software finds the closest voxel in the CT volume that matches specific parameters. The registration is then updated accordingly. If the process is iterative, the matched voxels may be aligned completely (ideally). If the process is continuous, a density function is used to weight the importance of that particular voxel match and the registration is adjusted, using frequency and/or density, a degree that is proportional to the weighted importance.

Figure 2:
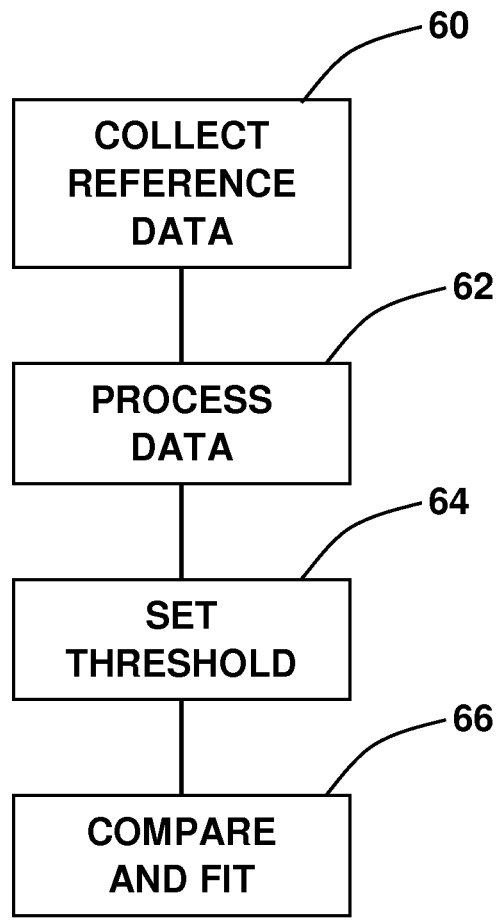
FIG. 2 is a flowchart of a more specific example of an embodiment of the method of FIG. 1.

Referring now to FIG. 2 for illustration purposes, there is shown a more specific example of an embodiment of the method of FIG. 1, which represents a binary voxel-based approach. At 60 a collection of reference data is taken, similar to the data acquisition step 20 described above. This step involves the acquisition of a plurality of CT scans, which are then assembled into a CT volume. The voxels representing internal lung air are then segmented from the CT volume using a known segmentation algorithm, obviating the need to extract the geometry, surfaces, or structures of the lung. During the procedure, the sensor is inserted into the lungs of the patient and a data stream is established between the sensor and a system processor.

At step 62, the data acquired from the sensor is processed, which involves de-cluttering and digitization. Each of the voxels is assigned a number based on the tissue density Housefield number. This density value can be associated with gray level or color using well known window-leveling techniques. The density is proportional to a probability that the sensor will occupy a given voxel. The data is also filtered as desired. For example, if the sensor is advanced slowly rather than quickly, it will necessarily result in higher densities as any one voxel is going to be occupied for a longer period of time while the sensor takes longer to pass through. Hence, an advancement rate may be noted and used to adjust the densities accordingly. After filtering, the voxels with higher densities are given higher registration importance than voxels having lower densities.

At step 64 a threshold value is set for the sensing volume voxels. For example, if the density of a given voxel is higher than the threshold value, that voxel is considered to be tissue and is given a value of zero. If the density of the voxel is below the threshold, that voxel is considered to be air and is given a value of 1. Hence the voxel space now becomes a binary voxel space. This function is performed both on the CT volume as well as on the sensor data.

At step 66 a compare and fit function is performed. Because a binary system is being used, it is possible to use a variety of matching methods to register the two binary volumes. For example, a subtraction method could be used. A subtraction method superimposes a segment of the sensor data over a corresponding segment of the binary CT volume. The registration is effected by subtracting the binary values of the one volume from the other. For example for any given voxel, if the values are both 1, when the aligned voxels are subtracted the value for that matched voxel space is zero. If they are not the same, however, subtraction results in either a 1 or a −1. All values are converted to their absolute values and totaled. The registration of that particular segment of sensor data is adjusted until a minimum subtracted total is acquired. One advantage of this method is that a minimum may be acquired regardless of image quality.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for registering a three-dimensional model of a body volume to a real-time indication of a sensor position, the method comprising:
    collecting reference data on the body volume;
    creating the three-dimensional model of said body volume from the reference data;
    inserting a sensor into a body lumen and recording location data from said sensor including a real-time sensor position;
    processing said location data recorded by the inserted sensor to form a three-dimensional shape corresponding to space within said lumen, the three-dimensional shape including a plurality of cavity voxels;
    assigning a value to each cavity voxel of the plurality of cavity voxels encountered by the sensor, the value of each cavity voxel corresponding to a frequency with which each cavity voxel encounters the sensor;
    adjusting a density of the plurality of cavity voxels in accordance with the value of each cavity voxel;
    creating clouds of cavity voxels having varying densities that match interior anatomical cavity features;
    defining a plurality of parameters having predefined thresholds;
    determining which of the cavity voxels of the plurality of cavity voxels identified by the location data satisfy the predefined thresholds of the plurality of parameters;
    selecting the cavity voxels satisfying the predefined thresholds of the plurality of parameters; and
    comparing said three-dimensional shape including only cavity voxels satisfying the predefined thresholds of the plurality of parameters to said three dimensional model to establish a feature-based registration.

2. The method of claim 1 wherein collecting reference data comprises acquiring a plurality of CT scans.

3. The method of claim 1 wherein creating the three-dimensional model of said body volume involves assembling a plurality of CT scans into a three-dimensional CT model.

4. The method of claim 1 wherein inserting the sensor into the body lumen and recording location data from said sensor comprises placing a catheter having said sensor at its distal tip into the body lumen, and recording position data from said sensor while moving said sensor within at least said body lumen.

5. The method of claim 1 wherein processing said location data comprises de-cluttering said location data.

6. The method of claim 5 wherein processing said location data further comprises digitizing said location data.

7. The method of claim 6 wherein processing said location data further comprises filtering said location data.

8. The method of claim 1 wherein cavity voxels with higher densities are given higher weight in registration than cavity voxels with lower densities.

9. The method of claim 1 wherein assigning values to cavity voxels of said location data involves assigning values based on tissue value Hounsfield numbers.

10. The method of claim 1 wherein defining parameters comprises defining a density range required for each cavity voxel of the plurality of cavity voxels.

11. The method of claim 1 wherein defining parameters comprises defining a proximity from an already-designated cavity voxel with cavity voxels satisfying the predefined thresholds of the plurality of parameters.

12. The method of claim 1 wherein defining parameters comprises defining a parameter template including multiple parameters.

13. The method of claim 12 wherein defining a parameter template involves defining the predefined thresholds of the plurality of parameters as follows:
    requiring the cavity voxels to have a certain density corresponding to air;
    requiring the cavity voxels to be located adjacent another cavity voxel having said certain density corresponding to air; and
    requiring the cavity voxels to be adjacent to cavity voxels having densities corresponding to blood vessels.

14. The method of claim 1 wherein the comparing step further includes the steps of:
    developing an initial guess;
    using said initial guess to establish said feature-based registration;
    calculating a difference between said three-dimensional model and said three-dimensional shape including only cavity voxels satisfying the predefined thresholds of the plurality of parameters;
    finding a closest cavity voxel in said three-dimensional model that matches parameters based on a cavity voxel visited by said sensor, each time said sensor encounters a new cavity voxel; and
    updating said feature-based registration as said sensor encounters new cavity voxels.

15. The method of claim 14 wherein said comparing step is iterative.

16. The method of claim 14 wherein said comparing step is continuous.

17. A method for registering a three-dimensional model of a lung volume to a real-time indication of a sensor position, the method comprising:
    collecting reference data on the lung volume;
    creating the three-dimensional model of said lung volume;
    inserting a sensor into an airway and recording location data from said sensor including a real-time sensor location;
    processing said location data;
    setting a threshold value for sensing volume voxels of the location data;
    forming a three-dimensional shape corresponding to space within said airway, the three-dimensional shape including a plurality of cavity voxels;
    assigning a value to each cavity voxel of the plurality of cavity voxels encountered by the sensor, the value of each cavity voxel corresponding to a frequency with which each cavity voxel encounters the sensor;

adjusting a density of the plurality of cavity voxels in accordance with the value of each cavity voxel;

creating clouds of cavity voxels having varying densities that match interior anatomical cavity features;

defining a plurality of parameters having predefined thresholds;

determining which of the cavity voxels of the plurality of cavity voxels identified by the location data satisfy the predefined thresholds of the plurality of parameters;

selecting the cavity voxels satisfying the predefined thresholds of the plurality of parameters; and comparing said three-dimensional shape including only cavity voxels satisfying the predefined thresholds of the plurality of parameters to said three dimensional model to establish a feature-based registration.

18. The method of claim 17 wherein collecting reference data comprises acquiring a plurality of CT scans.

19. The method of claim 17 wherein creating the three-dimensional model of said lung volume involves assembling a plurality of CT scans into a three-dimensional CT model.

20. The method of claim 19 wherein assembling the plurality of CT scans into a three-dimensional model involves segmenting voxels of the CT scan representing internal lung air.

21. The method of claim 17 wherein inserting the sensor into the airway and recording location data from said sensor comprises placing a catheter having said sensor at its distal tip into the airway, and recording position data from said sensor while moving said sensor within at least said airway.

22. The method of claim 17 wherein processing said location data comprises de-cluttering said location data.

23. The method of claim 22 wherein processing said location data further comprises digitizing said location data.

24. The method of claim 23 wherein processing said location data further comprises filtering said location data.

25. The method of claim 17 wherein cavity voxels with higher densities are given higher weight in registration than cavity voxels with lower densities.

26. The method of claim 17 wherein assigning values to cavity voxels of said location data involves assigning values based on tissue value Hounsfield numbers.

27. The method of claim 17 wherein forming a three-dimensional shape corresponding to space within said airway comprises forming a binary voxel space.

28. The method of claim 27 wherein creating a three-dimensional model of said lung volume comprises creating a binary voxel model of said lung volume.

29. The method of claim 28 wherein forming a binary voxel space comprises assigning a value of zero to all voxels having densities higher than said threshold value.

30. The method of claim 29 further comprising assigning all other voxels a value of 1 and considering those voxels having a value of 1 as representing air.

31. The method of claim 30 wherein comparing said three-dimensional shape to said three dimensional model comprises:

using a binary matching method to compare said three-dimensional shape including only cavity voxels satisfying the predefined thresholds of the plurality of parameters to said three dimensional model to establish the feature-based registration.

32. The method of claim 31 wherein using the binary matching method involves using a subtraction method.

33. The method of claim 32 wherein using the subtraction method involves superimposing a segment of the reference data over a corresponding segment of the location data.

* * * * *